United States Patent
Jung et al.

(10) Patent No.: US 11,596,322 B2
(45) Date of Patent: Mar. 7, 2023

(54) BIO-SIGNAL MEASURING APPARATUS AND BIO-SIGNAL MEASURING METHOD

(71) Applicant: SAMSUNG ELECTRONICS CO., LTD., Suwon-si (KR)

(72) Inventors: Myoung Hoon Jung, Bucheon-si (KR); Kak Namkoong, Seoul (KR); Yeol Ho Lee, Anyang-si (KR); Won Jong Jung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1088 days.

(21) Appl. No.: 16/202,276

(22) Filed: Nov. 28, 2018

(65) Prior Publication Data
US 2019/0167144 A1    Jun. 6, 2019

(30) Foreign Application Priority Data
Dec. 1, 2017  (KR) .................. 10-2017-0164563

(51) Int. Cl.
*A61B 5/00*    (2006.01)
*A61B 5/053*    (2021.01)
(Continued)

(52) U.S. Cl.
CPC ............ *A61B 5/053* (2013.01); *A61B 5/7278* (2013.01); *A61B 5/024* (2013.01); *A61B 5/0205* (2013.01);
(Continued)

(58) Field of Classification Search
CPC ....... A61B 5/053; A61B 5/4872; A61B 5/681; A61B 5/7221; A61B 2562/0214;
(Continued)

(56) References Cited

U.S. PATENT DOCUMENTS

| 7,079,889 B2 | 7/2006 | Nakada |
| 8,934,966 B2 | 1/2015 | Osawa |

(Continued)

FOREIGN PATENT DOCUMENTS

| EP | 1380256 A1 | 1/2004 | |
| EP | 1886626 A1 * | 2/2008 | ........... A61B 5/0537 |

(Continued)

OTHER PUBLICATIONS

Communication dated Feb. 19, 2019, from the European Patent Office in counterpart European Application No. 18209158.7.
(Continued)

*Primary Examiner* — Jeffrey P Aiello
(74) *Attorney, Agent, or Firm* — Sughrue Mion, PLLC

(57) ABSTRACT

A bio-signal measuring apparatus includes a first electrode, a second electrode, a third electrode, a fourth electrode, and a first circuit network and a second circuit network, each of the first circuit network and the second circuit network includes one or more resistances. The bio-signal measuring apparatus further includes an impedance measurer configured to measure a first impedance of the first circuit network in a first correction mode, measure a second impedance of the second circuit network in a second correction mode, measure a third impedance of an object in a first measurement mode, using the first electrode, the second electrode, the third electrode, and the fourth electrode, and measure a fourth impedance of the object in a second measurement mode, using the first electrode, the second electrode, the third electrode, and the fourth electrode.

31 Claims, 8 Drawing Sheets

(51) Int. Cl.
- *A61B 5/024* (2006.01)
- *A61B 5/08* (2006.01)
- *A61B 5/0295* (2006.01)
- *A61B 5/0205* (2006.01)
- *A61B 5/0245* (2006.01)
- *A61B 5/0265* (2006.01)
- *A61B 5/0537* (2021.01)
- *A61B 5/145* (2006.01)
- *A61B 5/1477* (2006.01)

(52) U.S. Cl.
CPC .......... *A61B 5/0245* (2013.01); *A61B 5/0265* (2013.01); *A61B 5/0295* (2013.01); *A61B 5/02405* (2013.01); *A61B 5/0537* (2013.01); *A61B 5/08* (2013.01); *A61B 5/0809* (2013.01); *A61B 5/1477* (2013.01); *A61B 5/14546* (2013.01); *A61B 5/4519* (2013.01); *A61B 5/4866* (2013.01); *A61B 5/4872* (2013.01); *A61B 5/4875* (2013.01); *A61B 2562/04* (2013.01)

(58) Field of Classification Search
CPC . A61B 5/0531; A61B 2562/04; A61B 5/0809; A61B 5/1477; A61B 5/0265; A61B 5/7225; A61B 5/0537; A61B 5/08; G01N 27/028; G01N 33/49; G01N 27/4163; G01N 33/66; G01N 27/02; G01N 33/48707; G01N 27/026; H03H 11/28; H03H 7/40; H03H 7/38; G01R 35/00; G01R 35/005; G01R 27/16
USPC ....... 324/601, 649, 713, 600, 692; 333/17.3; 600/547; 702/65, 85, 104, 19, 64, 75, 702/108, 22
See application file for complete search history.

(56) References Cited

U.S. PATENT DOCUMENTS

| | | | |
|---|---|---|---|
| 9,591,987 B1* | 3/2017 | Liedtke | A61B 5/0537 |
| 10,368,773 B2 | 8/2019 | Jung et al. | |
| 2004/0010205 A1* | 1/2004 | Nakada | A61B 5/053 |
| | | | 600/547 |
| 2008/0045854 A1* | 2/2008 | Weichao | A61B 5/0537 |
| | | | 600/547 |
| 2012/0194203 A1* | 8/2012 | Osawa | A61B 5/24 |
| | | | 324/649 |
| 2017/0100052 A1* | 4/2017 | Jung | A61B 5/4872 |
| 2017/0172452 A1* | 6/2017 | Lee | A61B 5/4875 |
| 2019/0167144 A1* | 6/2019 | Jung | A61B 5/7278 |

FOREIGN PATENT DOCUMENTS

| | | | |
|---|---|---|---|
| JP | 2012-157463 A | | 8/2012 |
| KR | 10-0437488 B1 | | 6/2004 |
| KR | 10-2008-0102581 A | | 11/2008 |
| KR | 10-2010-0108848 A | | 10/2010 |
| KR | 10-2012-0102201 A | | 9/2012 |
| KR | 10-1268498 B1 | | 6/2013 |
| KR | 10-1324560 B1 | | 11/2013 |
| KR | 20170026914 A | * | 8/2015 |
| KR | 10-2016-0046616 A | | 4/2016 |
| KR | 10-1689555 B1 | | 12/2016 |
| KR | 10-2017-0026914 A | | 3/2017 |
| KR | 10-2017-0041511 A | | 4/2017 |
| KR | 10-2017-0072700 A | | 6/2017 |

OTHER PUBLICATIONS

P. Ask et al. "ECG Electrodes. A Study of Electrical and Mechanical Long-term Properties" ACTA Anaesthesiologica Scandinav, vol. 23, No. 2, Jan. 1, 1979 (pp. 189-206).

Communication dated Oct. 25, 2022, issued by the Korean Intellectual Property Office in Korean Patent Application No. 10-2017-0164563

\* cited by examiner

BIO-SIGNAL MEASURING APPARATUS AND BIO-SIGNAL MEASURING METHOD

CROSS-REFERENCE TO RELATED APPLICATION(S)

This application claims priority from Korean Patent Application No. 10-2017-0164563, filed on Dec. 1, 2017, in the Korean Intellectual Property Office, the disclosure of which is incorporated herein by reference in its entirety.

BACKGROUND

1. Field

Apparatuses and methods consistent with embodiments relate to a bio-signal measuring apparatus and bio-signal measuring method.

2. Description of the Related Art

Various medical devices for diagnosing a health state of a patient are being developed. Utilizing medical equipment for measuring a bioelectric signal of a patient allows for more convenient, more timely resulting health diagnosis. This increase in efficiency may save time and money for both the patient and the health care provider.

As bio-impedance apparatus may be used for monitoring the health or emotional state of a living body. Various studies are being conducted to manufacture a bio-impedance measuring device in a smaller size while still providing a method of measuring the bio-impedance quickly and accurately.

SUMMARY

According to an aspect of an embodiment, there is provided a bio-signal measuring apparatus, including a first electrode, a second electrode, a third electrode, a fourth electrode, and a first circuit network and a second circuit network, each of the first circuit network and the second circuit network includes one or more resistances. The bio-signal measuring apparatus further includes an impedance measurer configured to measure a first impedance of the first circuit network in a first correction mode, measure a second impedance of the second circuit network in a second correction mode, measure a third impedance of an object in a first measurement mode, using the first electrode, the second electrode, the third electrode, and the fourth electrode, and measure a fourth impedance of the object in a second measurement mode, using the first electrode, the second electrode, the third electrode, and the fourth electrode. The bio-signal measuring apparatus further includes a parameter obtainer configured to obtain an internal parameter of the impedance measurer, based on the first impedance of the first circuit network in the first correction mode and the second impedance of the second circuit network in the second correction mode, and a bio-impedance obtainer configured to obtain a bio-impedance of the object, based on the internal parameter, the third impedance of the object in the first measurement mode, and the fourth impedance of the object in the second measurement mode.

The first circuit network and the second circuit network may be configured as a single circuit.

The first circuit network and the second circuit network may be configured separately as independent circuits.

In the first correction mode, the impedance measurer may be connected to the first circuit network and further configured to apply a current to the first circuit network through a first terminal corresponding to the first electrode and a second terminal corresponding to the second electrode, and measure the first impedance by measuring a voltage produced between a third terminal corresponding to the third electrode and a fourth terminal corresponding to the fourth electrode.

In the second correction mode, the impedance measurer may be connected to the second circuit network and further configured to apply a current to the second circuit network through a first terminal corresponding to the first electrode and a second terminal corresponding to the second electrode, and measure the second impedance by measuring a voltage produced between a third terminal corresponding to the third electrode and a fourth terminal corresponding to the fourth electrode.

The first measurement mode may use a four-point measurement method of measuring an impedance, using the first electrode, the second electrode, the third electrode, and the fourth electrode, and the second measurement mode may use a two-point measurement method of measuring an impedance, using short-circuits of a combination of the first electrode, the second electrode, the third electrode, and the fourth electrode.

In the first measurement mode, the impedance measurer may be connected to the first electrode, the second electrode, the third electrode, and the fourth electrode, and further configured to apply a current to the object through the first electrode and the second electrode, and measure the third impedance by measuring a voltage produced between the third electrode and the fourth electrode.

In the second measurement mode, the impedance measurer is connected to the first electrode, the second electrode, the third electrode, and the fourth electrode, short-circuits the first electrode to the third electrode and short-circuits the second electrode to the fourth electrode, and is further configured to apply a current to the object through the first electrode and the second electrode, and measure the fourth impedance by measuring a voltage produced between the third electrode and the fourth electrode.

The internal parameter may include an input impedance and an output impedance.

The bio-impedance obtainer may use a bio-impedance calculation formula defining a relationship between the internal parameter of the impedance measurer, the third impedance, the fourth impedance, and the bio-impedance.

The bio-impedance calculation formula may be obtained by measuring a contact impedance when each electrode contacts the object.

The impedance measurer may be further configured to measure the first impedance and the second impedance by changing a frequency of an input current.

The parameter obtainer may be further configured to obtain the internal parameter for each frequency of the impedance measurer, based on the first impedance and the second impedance that are measured for each frequency of the input current.

The apparatus may further include a storage part configured to store the internal parameter for each frequency of the impedance measurer.

The apparatus may further include a mode setter configured to generate a control signal for setting an operation mode of the bio-signal measuring apparatus.

The apparatus may further include a bio-information obtainer configured to obtain bio-information of the object based on the bio-impedance of the object.

The bio-information may include any one or any combination of body fat mass, fat-free mass, muscle mass, skeletal muscle mass, basal metabolism, intracellular water, extracellular water, total body water, mineral content, visceral fat, blood flow, respiration, heart rate, and heart rate variability.

According to an aspect of an embodiment, there is provided a bio-signal measuring method, including measuring a first impedance of a first circuit network in a first correction mode, measuring a second impedance of a second circuit network in a second correction mode, and obtaining an internal parameter of an impedance measurer, based on the first impedance of the first circuit network in the first correction mode and the second impedance of the second circuit network in the second correction mode. The method further includes measuring a third impedance of an object in a first measurement mode, measuring a fourth impedance of the object in a second measurement mode, and obtaining a bio-impedance of the object, based on the internal parameter, the third impedance of the object in the first measurement mode, and the fourth impedance of the object in the second measurement mode.

Each of the first circuit network and the second circuit network may include one or more resistances.

The first circuit network and the second circuit network may be configured as a single circuit.

The first circuit network and the second circuit network may be configured separately as independent circuits.

The measuring of the first impedance may include entering the first correction mode, connecting the impedance measurer to the first circuit network, applying a current to the first circuit network through a first terminal and a second terminal of the impedance measurer, measuring a voltage produced between a third terminal and a fourth terminal of the impedance measurer, and obtaining the first impedance based on the current and the voltage.

The measuring of the second impedance may include based on the measuring the first impedance being completed, entering the second correction mode, connecting the impedance measurer to the second circuit network, applying a current to the first circuit network through a first terminal and a second terminal of the impedance measurer, measuring a voltage produced between a third terminal and a fourth terminal of the impedance measurer, and obtaining the second impedance based on the current and the voltage.

The first measurement mode may use a four-point measurement method of measuring an impedance, using four electrodes, and the second measurement mode may use a two-point measurement method of measuring an impedance, using short-circuits of a combination of the four electrodes.

The measuring of the third impedance may include entering the first correction mode, connecting a first terminal of the impedance measurer to a first electrode, a second terminal of the impedance measurer to a second electrode, a third terminal of the impedance measurer to a third electrode, and a fourth terminal of the impedance measurer to a fourth electrode, applying a current to the object through the first electrode and the second electrode, measuring a voltage produced between the third electrode and the fourth electrode, and obtaining the third impedance based on the current and the voltage.

The measuring of the fourth impedance may include based on the measuring the third impedance being completed, entering the second measurement mode, based on the measurement of the third impedance being completed, short-circuiting a first electrode to a third electrode, and short-circuiting a second electrode to a fourth electrode, applying a current to the object through the first electrode and the second electrode, measuring a voltage produced between the third electrode and the fourth electrode, and obtaining the fourth impedance based on the current and the voltage.

The internal parameter may include an input impedance and an output impedance.

The obtaining of the bio-impedance of the object may include obtaining the bio-impedance of the object by using a bio-impedance calculation formula which defines a relationship between the internal parameter of the impedance measurer, the third impedance, the fourth impedance, and the bio-impedance.

The bio-impedance calculation formula may be obtained by considering a contact impedance, which occurs when each electrode contacts the object.

The method may further include obtaining bio-information of the object based on the bio-impedance of the object.

The bio-information may include any one or any combination of body fat mass, fat-free mass, muscle mass, skeletal muscle mass, basal metabolism, intracellular water, extracellular water, total body water, mineral content, visceral fat, blood flow, respiration, heart rate, and heart rate variability.

DETAILED DESCRIPTION

Figure 1:
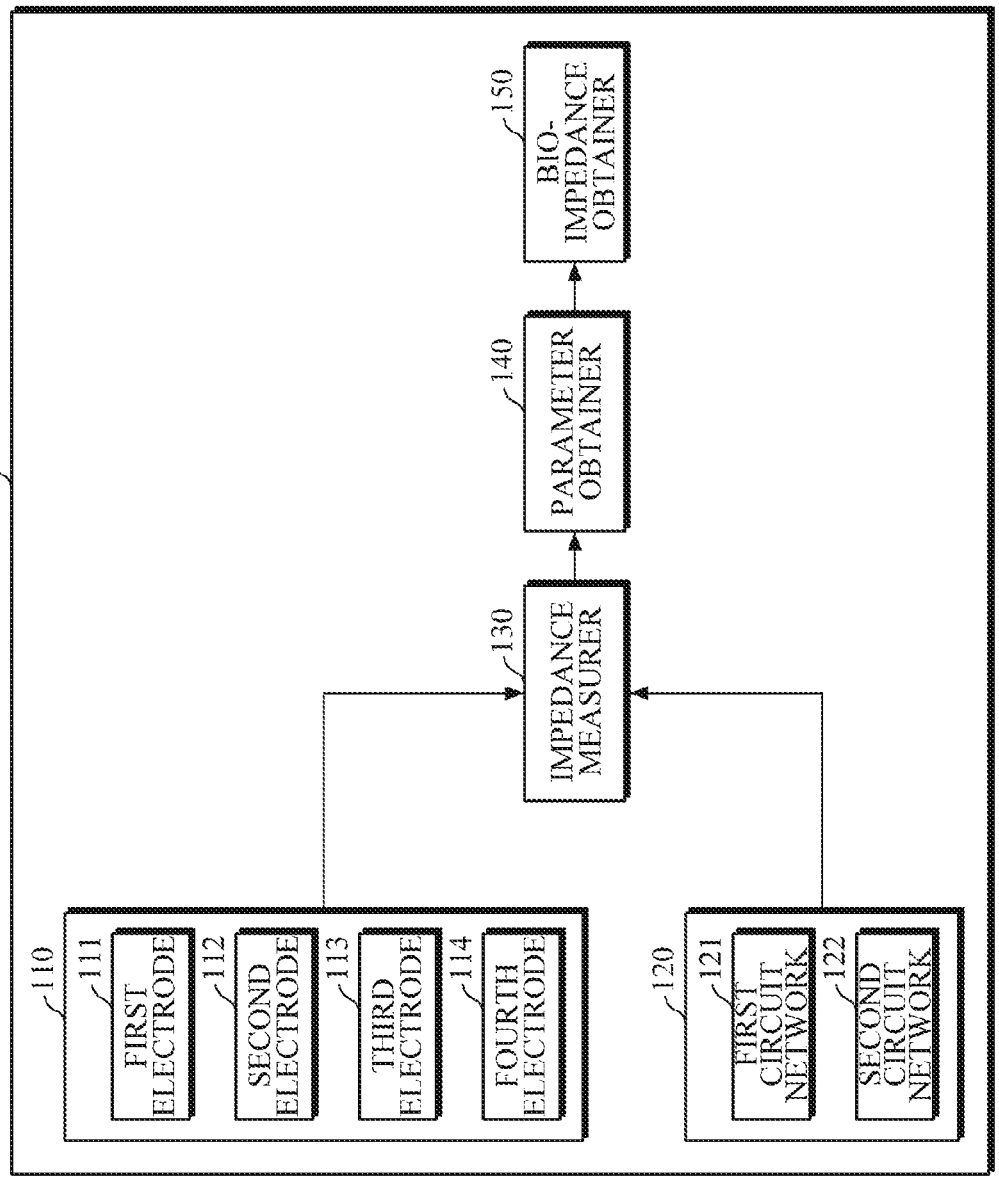
FIG. 1 is a block diagram illustrating an example of a bio-signal measuring apparatus.

Hereinafter, embodiments of the disclosure will be described in greater detail with reference to the accompanying drawings. In the following description, like drawing reference numerals are used for like elements, even in different drawings. The matters defined in the description, such as detailed construction and elements, are provided to assist in a comprehensive understanding of the embodiments. However, it is apparent that the embodiments can be practiced without those specifically defined matters. Also, a detailed description of well-known functions and configurations incorporated may be omitted when they would obscure the description with unnecessary detail.

Process steps described may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to embodiments, and can be varied according to a purpose of a user, manager, precedent and so on. Therefore, definitions of the terms may be made on the basis of the overall context.

It will be understood that, although the terms first, second, etc. may be used to describe various elements, these elements may not be limited by these terms. These terms are only used to distinguish one element from another. Any references to 'singular' r ray include plural unless expressly stated otherwise. In the present specification, it may be understood that the terms, such as 'including' or 'having,' etc., are intended to indicate the existence of the features, numbers, steps, actions, components, parts, or combinations thereof disclosed in the specification, e not intended to preclude the possibility that one or more other features, numbers, steps, actions, components, parts, or combinations thereof may exist or may be added.

Further, components that will be described in the specification are disseminate according to functions mainly performed by the components. That is, two or more components can be integrated into a single component. Furthermore, a single component can be separated into two or more components. Moreover, each component can additionally perform some or all of a function executed by another component in addition to the main function thereof. Some or all of the main functions of each component can be carried out by another component. Each component may be implemented as hardware, software, or a combination of both.

FIG. 1 is a block diagram illustrating an example of a bio-signal measuring apparatus. The bio-signal measuring apparatus 100 of FIG. 1 may be embedded in an electronic device. In this case, examples of the electronic device may include a cellular phone, a smartphone, a tablet PC, a laptop computer, a personal digital assistant (PDA), a portable multimedia player (PMP), a navigation system, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device and the wearable device are not limited thereto.

The bio-signal measuring apparatus 100 is an apparatus that may measure bio-impedance of an object by using Bioelectrical Impedance Analysis (BIA), and may support a correction mode and a measurement mode. Here, the correction mode is a mode for obtaining an internal parameter (e.g., input impedance, output impedance, etc.) of an impedance measurer 130 to accurately measure a bio-impedance; and the measurement mode is a mode for obtaining a bio-impedance of an object by using the internal parameter of the impedance measurer 130, which is obtained in the correction mode.

Referring to FIG. 1, the bio-signal measuring apparatus may 100 include an electrode part 110, a circuit network part 120, an impedance measurer 130, a parameter obtainer 140, and a bio-impedance obtainer 150.

The electrode part 110 may be configured to include four electrodes 111 through 114, which come into contact with an object. The first electrode 111 and the second electrode 112, which are current applying electrodes, are used to apply a measurable current to the object; the third electrode 113 and the fourth electrode 114, which are voltage measuring electrodes, are used to measure a voltage applied to the object due to the measurable current applied through the first electrode 111 and the second electrode 112.

In the embodiment in which the bio-signal measuring apparatus 100 is implemented in a wearable device, and when the user wears the wearable device, the electrodes 111 through 114 of the electrode part 110 may be adapted to naturally come into contact with body parts of a user or some of the electrodes 111 through 114 may naturally come into contact with the body parts of the user, and other electrodes may be adapted to contact the body parts by action of the user.

The circuit network part 120 may be configured to include a first circuit network 121 and a second circuit network 122, each of which will include at least one or more resistances. The circuit network part 120 is used to measure the internal parameter (e.g., input impedance, output impedance, etc.) of the impedance measurer 130, and may be connected to the impedance measurer 130 in a first correction mode and a second correction mode.

The first circuit network 121 and the second circuit network 122 may be configured as a single circuit, the structure of which may be changed by an internal switch and the like. Further, the first circuit network 121 and the second circuit network 122 may be configured separately as independent circuits.

The impedance measurer 130 may be connected to the circuit network part 120 or to the electrode part 110 according to an operation mode of the bio-signal measuring apparatus 100.

In one embodiment, the impedance measurer 130 may be configured to connect to the first circuit network 121, in the first correction mode, to measure an impedance (hereinafter referred to as a first impedance) of the first circuit network 121 The impedance measurer 130 may also be configured to connect to the second circuit network 122, in the second correction mode, to measure an impedance (hereinafter referred to as a second impedance) of the second circuit network 122.

An embodiment of the impedance measurer 130 in the first correction mode and the second correction mode will be described below.

In the first correction mode, when the bio-signal measuring apparatus 100 enters the first correction mode, according to a predetermined control signal, the impedance measurer 130 may connect four terminals (a first terminal through a fourth terminal), which correspond to the four electrodes 111 through 114, to the first circuit network 121. The impedance measurer 130 may apply a current to the first circuit network 121, through the first terminal corresponding to the first electrode 111 and the second terminal corresponding to the second electrode 112; may then measure a voltage produced by the applied current between the third terminal corresponding to the third electrode 113 and the fourth terminal corresponding to the fourth electrode 114; and may obtain the first impedance of the first circuit network 121 by using a relational expression, $V = I \times Z$, among the voltage V, the current I, and the impedance Z.

In the second correction mode, upon completing measurement of the first impedance of the first circuit network 121, in the first correction mode, the bio-signal measuring apparatus 100 may enter the second correction mode according to a predetermined control signal. The impedance measurer 130 may connect the four terminals (the first terminal through the fourth terminal) to the second circuit network 122 in the second correction mode. The impedance measurer 130 may apply a current to the second circuit network 122 through the first terminal and the second terminal; may measure a voltage produced by the applied current between the third terminal and the fourth terminal; and may obtain the second impedance of the second circuit network 122 by using a relational expression, $V = I \times Z$, among the voltage V, the current I, and the impedance Z.

In this embodiment, the connection of the impedance measurer 130 to the second circuit network 122 may include not only an embodiment in which the impedance measurer 130 physically breaks connection with the first circuit network 121, and physically makes connection with the second circuit network 122, which is separate from the first circuit network 121, but also an embodiment in which, while the impedance measurer 130 is connected to any one circuit, an internal structure of the circuit is changed so that the first circuit network 121 is changed to the second circuit network 122.

In one embodiment, the impedance measurer 130 may be connected to the four electrodes, 111 through 114, in a first measurement mode and a second measurement mode to measure an impedance of an object. For example, in the first measurement mode, the impedance measurer 130 may measure an impedance (hereinafter referred to as a third impedance) of the object by using a four-point measurement method using four electrodes; and in the second measurement mode, the impedance measurer 130 may measure an impedance (hereinafter referred to as a fourth impedance) of the object by using a two-point measurement method using short-circuits of a combination of the four electrodes.

In the first measurement mode, when the bio-signal measuring apparatus 100 enters the first measurement mode according to a predetermined control signal, the impedance measurer 130 may connect the first terminal to the first electrode 111, the second terminal to the second electrode 112, the third terminal to the third electrode 113, and the fourth terminal to the fourth electrode 114. The impedance measurer 130 may apply a current to the object through the first electrode 111 and the second electrode 112; may measure a voltage produced by the applied current between the third electrode 113 and the fourth electrode 114; and may obtain the third impedance of the object by using a relational expression, V=I×Z, among the voltage V, the current I, and the impedance Z.

Upon completing measurement of the third impedance of the object in the first measurement mode, the bio-signal measuring apparatus 100 may enter the second measurement mode according to a predetermined control signal. The impedance measurer 130 may short-circuit the first electrode 111 to the third electrode 113, and may short-circuit the second electrode 112 to the fourth electrode 114. The impedance measurer 130 may apply a current to the object through the first electrode 111 and the second electrode 112; may measure a voltage produced by the applied current between the third electrode 113 and the fourth electrode 114; and may obtain the fourth impedance of the object by using a relational expression, V=I×Z, among the voltage V, the current I, and the impedance Z.

The parameter obtainer 140 may obtain an internal parameter of the impedance measurer 130 based on the first impedance and the second impedance. Here, the internal parameter may include an input impedance and an output impedance. The impedance measurer 130 may be represented by an equivalent circuit including a current source, an output impedance connected in parallel with the current source, a voltmeter, and an input impedance connected in parallel with the voltmeter. In this embodiment, a first impedance relational expression and a second impedance relational expression may be obtained based on the equivalent circuit of the impedance measurer 130, an equivalent circuit of the first circuit network, and an equivalent circuit of the second circuit network. The parameter obtainer 140 may obtain the input impedance and the output impedance by using the first impedance relational expression, the second impedance relational expression, the measured first impedance value, and the measured second impedance value.

The bio-impedance obtainer 150 may obtain a bio-impedance of an object by using the internal parameter (e.g., the input impedance and the output impedance) of the impedance measurer 130, the third impedance and the fourth impedance. In one embodiment, the bio-impedance obtainer 150 may obtain the bio-impedance of the object by using a bio-impedance calculation formula. In this case, the bio-impedance calculation formula defines a relationship between the internal parameter of the impedance measurer 130, the third impedance, the fourth impedance, and the bio-impedance, and may be obtained by considering a contact impedance which occurs when each electrode and the object contact each other. For example, the bio-impedance may be represented by the following Equation 1.

$$Z_m = Z_{4P} \times \frac{(a+Z_i)(a+Z_s)}{Z_{4P}(2a+Z_i+Z_s)+Z_iZ_s}, \quad \text{[Equation 1]}$$

$$a = \frac{2}{\frac{1}{Z_{2P}} - \frac{1}{Z_i} - \frac{1}{Z_s}}$$

Here, $Z_m$ denotes the bio-impedance of the object, $Z_{4P}$ denotes the third impedance, $Z_{2P}$ denotes the fourth impedance, $Z_i$ denotes the input impedance of the impedance measurer 130, and $Z_s$ denotes the output impedance of the impedance measurer 130.

In one embodiment, the impedance measurer 130 may measure the first impedance of the first circuit network 121 and the second impedance of the second circuit network 122, by changing a frequency of an input current. In this case, the parameter obtainer 140 may obtain an internal parameter for each frequency of the impedance measurer 130 based on the first impedance and the second impedance, which are measured for each frequency, and may store the internal parameter for each frequency of the impedance measurer 130 in an internal or external database of the bio-signal measuring apparatus 100. The stored internal parameter for each frequency may be used to obtain the bio-impedance for each frequency.

Figure 2:
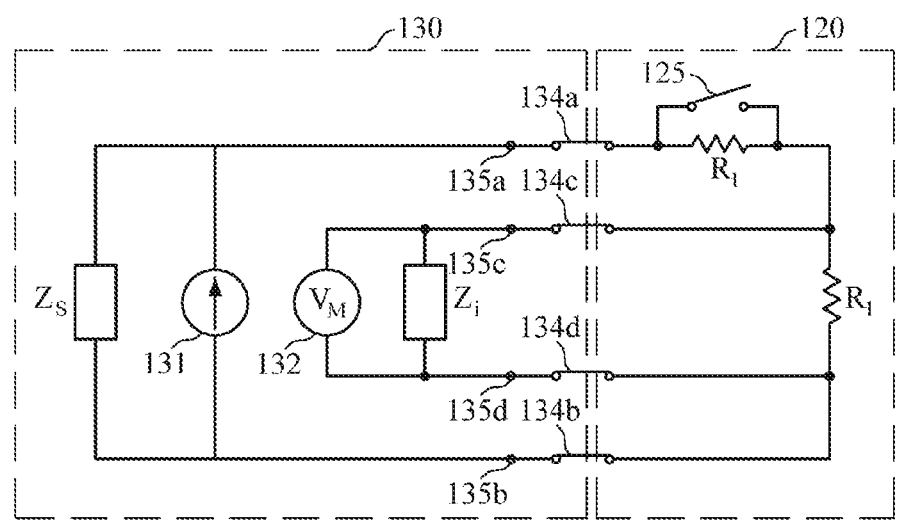
FIG. 2 is a diagram illustrating an example of a first circuit network and a second circuit network.

FIG. 2 is a diagram illustrating an example of a first circuit network and a second circuit network.

Referring to FIG. 2, the impedance measurer 130 may be represented by a current source 131, which applies a current through a first terminal 135a and a second terminal 135b, an output impedance $Z_s$, which is connected in parallel with the current source 131, a voltmeter 132, which measures a voltage produced between a third terminal 135c and a fourth terminal 135d, and an input impedance $Z_i$, which is connected in parallel with the voltmeter 132. Further, the circuit network part 120 may be implemented as a single circuit, the internal structure of which may be changed by a switch 125, in which the first circuit network may show a state in which the switch 125 is opened, and the second circuit network may show a state in which the switch 125 is closed. That is, the first circuit network may include two resistances $R_1$ having the same resistance, and the second circuit network may include one resistance $R_1$.

Once the bio-signal measuring apparatus enters the first correction mode, according to a predetermined control signal, the impedance measurer 130 may connect the terminals 135a through 135d to the circuit network part 120 through the internal switches 134a through 134d to measure the first impedance of the first circuit network. Further, upon completing the measurement of the first impedance of the first circuit network, the bio-signal measuring apparatus may enter the second correction mode according to a predetermined control signal. Once the bio-signal measuring apparatus enters the first correction mode, the switch 125 of the circuit network part 120 is closed, such that the first circuit network is changed to the second circuit network, and the impedance measurer 130 may measure the second impedance of the second circuit network.

In this case, the first impedance of the first circuit network and the second impedance of the second circuit network may be obtained by dividing a measured voltage $V_f$ of the voltmeter 132 by an applied current I of the current source 131, in which the first impedance $Z_i$ may be represented by the following Equation 2, and the second impedance $Z_2$ may be represented by following Equation 3.

$$Z_1 = \frac{1}{\frac{1}{Z_S} + \frac{1}{R_1 + \frac{1}{\frac{1}{Z_i} + \frac{1}{R_1}}}} \times \frac{\frac{1}{Z_i} + \frac{1}{R_1}}{R_i + \frac{1}{\frac{1}{Z_i} + \frac{1}{R_1}}} \quad \text{[Equation 2]}$$

$$Z_2 = \frac{1}{\frac{1}{Z_s} + \frac{1}{Z_i} + \frac{1}{R_1}} \quad \text{[Equation 3]}$$

In Equations 2 and 3, the resistance $R_1$ is a known value, and the first impedance $Z_1$ and the second impedance $Z_2$ are values obtained by measurement, such that the parameter obtainer 140 may obtain the output impedance and the input impedance by using Equations 2 and 3.

Although FIG. 2 illustrates an embodiment in which the first circuit network and the second circuit network are implemented as a single circuit, the embodiment is not intended to be limiting. That is, the first circuit network and the second circuit network may be implemented separately as independent circuits.

Figure 3:
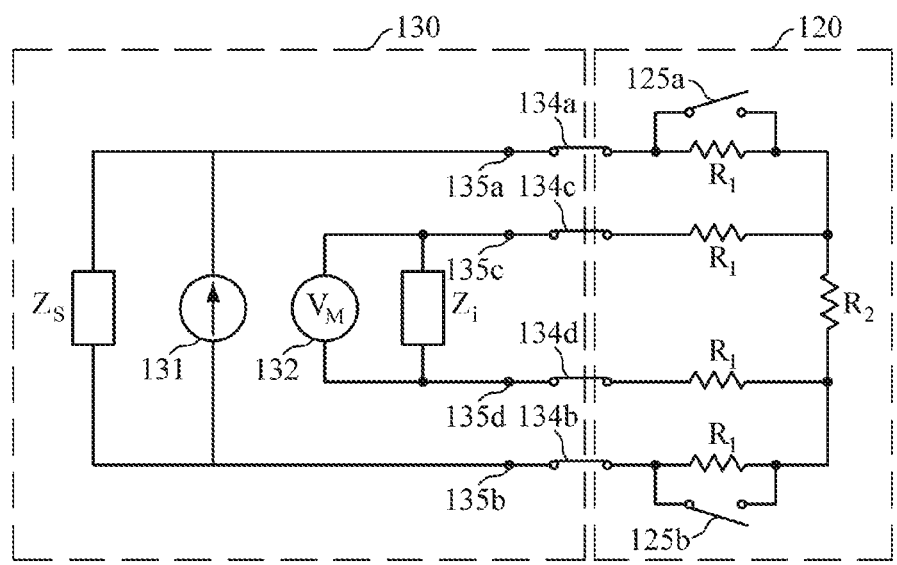
FIG. 3 is a diagram illustrating another example of a first circuit network and a second circuit network.

FIG. 3 is a diagram illustrating another example of a first circuit network and a second circuit network.

Referring to FIG. 3, a circuit network part 120 may be implemented as a single circuit, the internal structure of which may be changed by switches 125a and 125b, in which the first circuit network may show a state in which the switches 125a and 125b are opened, and the second circuit network may show a state in which the switches 125a and 125b are closed. That is, the first circuit network may include four resistances $R_1$ having the same resistance and one resistance $R_2$ having a different resistance. The second circuit network may include two resistances $R_1$ having the same resistance and one resistance $R_2$ having a different resistance.

Once the bio-signal measuring apparatus enters the first correction mode according to a predetermined control signal, the impedance measurer 130 may connect terminals 135a through 135d to the circuit network part 120 through internal switches 134a through 134d to measure the first impedance of the first circuit network. Further, upon completing measurement of the first impedance of the first circuit network, the bio-signal measuring apparatus may enter the second correction mode, according to a predetermined control signal. When the bio-signal measuring apparatus enters the first correction mode, the switches 125a and 125b of the circuit network part 120 are closed, such that the first circuit network is changed to the second circuit network, and the impedance measurer 130 may measure the second impedance of the second circuit network.

In this first correction mode, the first impedance of the first circuit network and the second impedance of the second circuit network may be obtained by dividing a measured voltage $V_m$ of the voltmeter 132 by an applied current I of the current source 131, in which the first impedance $Z_1$ may be represented by the following Equation 4, and the second impedance $Z_2$ may be represented by the following Equation 5.

$$Z_1 = R_2 \times \frac{1}{1 + \frac{R_2 + 2R_1}{Z_i}} \times \frac{Z_S}{Z_S + 2R_1 + \frac{1}{\frac{1}{R_2} + \frac{1}{2R_1 + Z_i}}} \quad \text{[Equation 4]}$$

$$Z_2 = R_2 \times \frac{1}{1 + \frac{R_2 + 2R_1}{Z_i}} \times \frac{Z_S}{Z_S + \frac{1}{\frac{1}{R_2} + \frac{1}{Z_i}}} \quad \text{[Equation 5]}$$

In Equations 4 and 5, the resistances $R_1$ and $R_2$ are known values, and the first impedance $Z_1$ and the second impedance $Z_2$ are values obtained by measurement, such that the parameter obtainer 140 may obtain the output impedance $Z_s$ and the input impedance $Z_i$ by using Equations 4 and 5.

Although FIG. 3 illustrates an embodiment in which the first circuit network and the second circuit network are implemented as a single circuit, the embodiment is not intended to be limiting. That is, the first circuit network and the second circuit network may be implemented separately as independent circuits.

Figure 4:
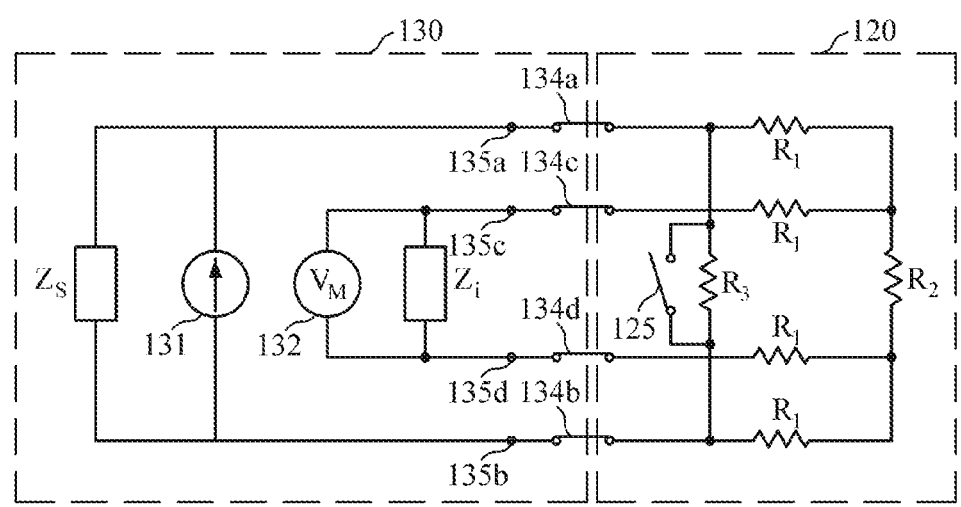
FIG. 4 is a diagram illustrating yet another example of a first circuit network and a second circuit network.

FIG. 4 is a diagram illustrating yet another example of a first circuit network and a second circuit network.

Referring to FIG. 4, a circuit network part 120 may be implemented as a single circuit, the internal structure of which may be changed by a switch 125, in which the first circuit network may show a state in which the switch 125 is opened, and the second circuit network may show a state in which the switch 125 is closed. That is, the first circuit network may include four resistances $R_1$ having the same resistance and two resistances $R_2$ and $R_3$ having different resistances; and the second circuit network may include two resistances $R_1$ having the same resistances and one resistance $R_2$ having a different resistance.

Once the bio-signal measuring apparatus enters the first correction mode, according to a predetermined control signal, the impedance measurer 130 may connect terminals 135a through 135d to the circuit network part 120 through internal switches 134a through 134d to measure the first impedance of the first circuit network. Further, upon completing measurement of the first impedance of the first circuit network, the bio-signal measuring apparatus may enter the second correction mode, according to a predetermined control signal. When the bio-signal measuring apparatus enters the first correction mode, the switch 125 of the circuit network part 120 is closed, such that the first circuit network is changed to the second circuit network, and the impedance measurer 130 may measure the second impedance of the second circuit network.

In this first correction mode, the first impedance of the first circuit network and the second impedance of the second circuit network may be obtained by dividing a measured voltage $V_{iTi}$ of the voltmeter 132 by an applied current of the current source 131, in which the first impedance $Z_1$ may be represented by the following Equation 6, and the second impedance $Z_2$ may be represented by the following Equation 7.

$$Z_1 = R_2 \times \frac{1}{1 + \frac{R_2 + 2R_1}{Z_i}} \times \frac{\frac{1}{Z_S} + \frac{1}{R_3}}{\frac{1}{\frac{1}{Z_S} + \frac{1}{R_3}} + 2R_1 + \frac{1}{\frac{1}{R_2} + \frac{1}{2R_1 + Z_i}}} \quad \text{[Equation 6]}$$

$$Z_2 = R_2 \times \frac{1}{1 + \frac{R_2 + 2R_1}{Z_i}} \times \frac{Z_S}{Z_S + 2R_1 + \frac{1}{\frac{1}{R_2} + \frac{1}{2R_1 + Z_i}}} \quad \text{[Equation 7]}$$

In Equations 6 and 7, the resistances $R_1$, $R_2$, and $R_3$ are known values, and the first impedance $Z_1$ and the second impedance $Z_2$ are values obtained by measurement, such that the parameter obtainer 140 may obtain the output impedance $Z_s$ and the input impedance $Z_i$ by using Equations 6 and 7.

Although FIG. 4 illustrates an embodiment in which the first circuit network and the second circuit network are implemented as a single circuit, the embodiment is not intended to be limiting. That is, the first circuit network and the second circuit network may be implemented separately as independent circuits.

Further, the first circuit network and the second circuit network illustrated in FIGS. 2 to 4 are embodiments. That is, the number of resistances included in the first circuit network and the second circuit network is not limited, and in the case in which the first circuit network and the second circuit network are not the same, they may be configured to have various circuit structures.

Figure 5:
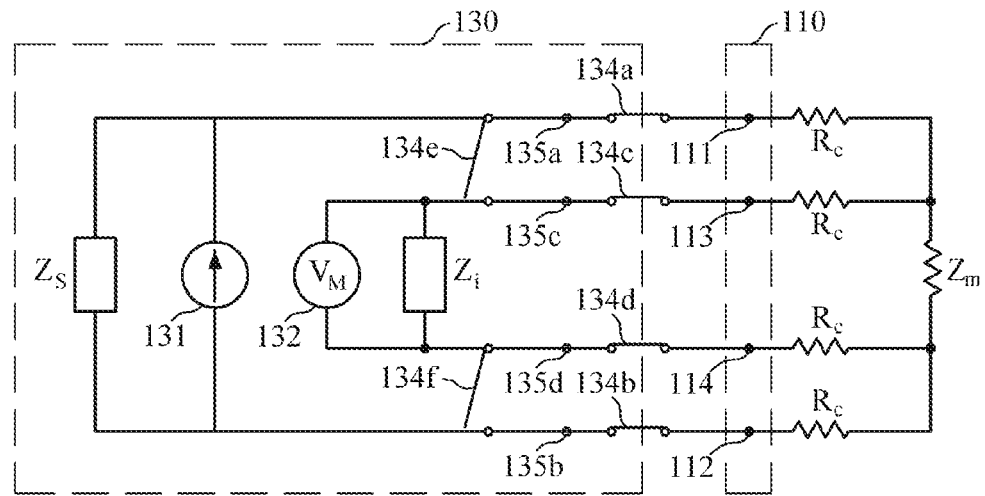
FIG. 5 is a circuit diagram explaining an example of an operation in a measurement mode.

FIG. 5 is a circuit diagram explaining an example of an operation in measurement modes. In FIG. 5, $Z_m$ is a bio-impedance of an object, $R_c$ is a contact impedance, which occurs when electrodes 111 through 114 contact the object, $R_c$ is an input impedance of an impedance measurer 130, and $Z_s$ is an output impedance of the impedance measurer 130.

Once the bio-signal measuring apparatus enters the first measurement mode according to a predetermined control signal, the impedance measurer 130 may connect terminals 135a through 135d to the electrodes 111 through 114 of the electrode part 110 through internal switches 134a through 134d to measure the third impedance of the object. Further, upon completing measurement of the third impedance of the object, the bio-signal measuring apparatus may enter the second measurement mode according to a predetermined control signal, and the impedance measurer 130 may close switches 134e and 134f to measure the fourth impedance of the object.

In the first measurement mode, the first electrode 111 and the third electrode 113, and the second electrode 112 and the fourth electrode 114 are opened, such that a relational expression of the third impedance of the object may be represented by the following Equation 8.

$$Z_{4P} = Z_m \times \frac{1}{1 + \frac{Z_m + 2R_c}{Z_i}} \times \frac{Z_s}{Z_s + 2R_c + \frac{1}{\frac{1}{z_m} + \frac{1}{2R_c + Z_i}}} \quad \text{[Equation 8]}$$

Further, in the second measurement mode, the first electrode 111 is short-circuited to the third electrode 113, and the second electrode 112 is short-circuited to the fourth electrode 114, such that a relational expression of the fourth impedance of the object may be represented by the following Equation 9.

$$Z_{2P} = \frac{1}{\frac{1}{Z_m + R_c} + \frac{1}{Z_i} + \frac{1}{R_s}} \quad \text{[Equation 9]}$$

In Equations 8 and 9, the third impedance $Z_{4P}$ and the fourth impedance $Z_{2P}$ are known values, and the input impedance $Z_i$ of the impedance measurer 130 and the output impedance $Z_s$ of the impedance measurer 130 are values obtained in the first and second correction modes. Thus, the bio-impedance $Z_m$ may be obtained by combining Equations 8 and 9.

A bio-impedance calculation formula derived from Equations 8 and 9 is the same as the above Equation 1.

Figure 6:
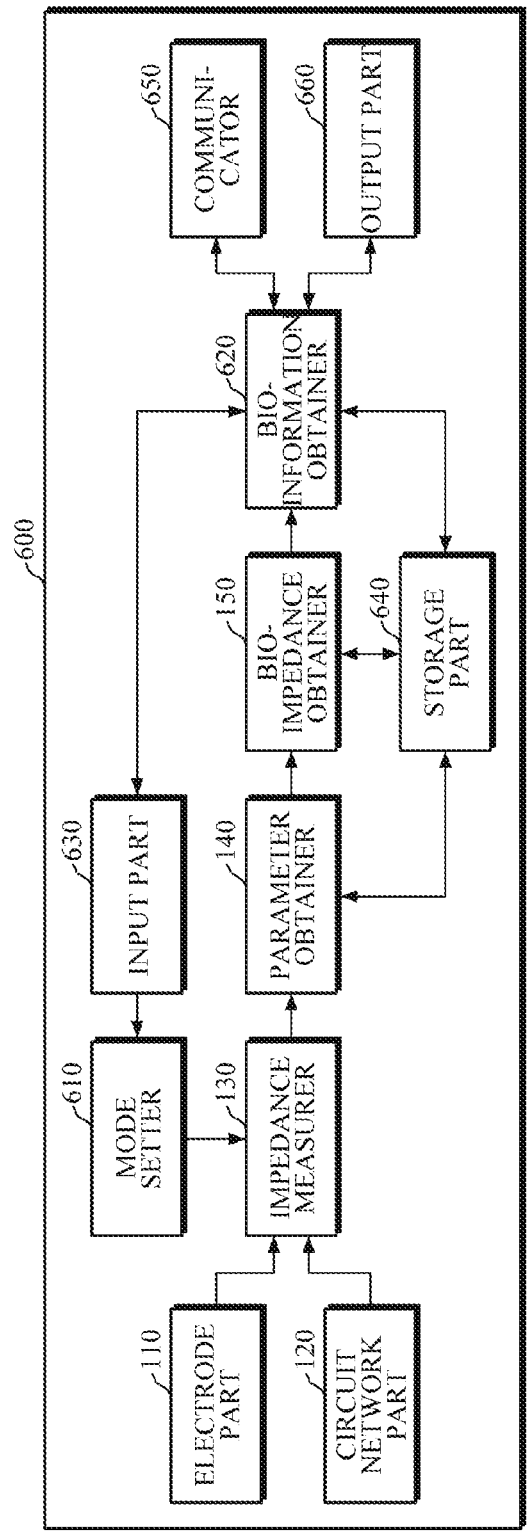
FIG. 6 is a block diagram illustrating another example of a bio-signal measuring apparatus.

FIG. 6 is a block diagram illustrating another example of a bio-signal measuring apparatus. The bio-signal measuring apparatus 600 of FIG. 6 may be embedded in an electronic device. In this case, examples of the electronic device may include a cellular phone, a smartphone, a tablet PC, a laptop computer, a personal digital assistant (PDA), a portable multimedia player (PMP), a navigation system, an MP3 player, a digital camera, a wearable device, and the like. Examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device and the wearable device are not limited thereto.

Referring to FIG. 6, the bio-signal measuring apparatus 600 includes an electrode part 110, a circuit network part 120, an impedance measurer 130, a parameter obtainer 140, a bio-impedance obtainer 150, a mode setter 610, a bio-information obtainer 620, an input part 630, a storage part 640, a communicator 650, and an output part 660. Here, the electrode part 110, the circuit network part 120, the impedance measurer 130, the parameter obtainer 140, and the bio-impedance obtainer 150 are described above with reference to FIGS. 1 to 5, such that a detailed description thereof will be omitted.

The mode setter 610 may generate a control signal for setting an operation mode of the bio-signal measuring apparatus 600. In this case, an operation mode of the bio-signal measuring apparatus 600 may include the first correction mode, the second correction mode, the first measurement mode, and the second measurement mode.

The mode setter 610 may generate a control signal for setting an operation mode of the bio-signal measuring apparatus 600 to the first correction mode according to a predetermined cycle, a user's instruction, a specific event (e.g., a device is on, etc.), and the like. Upon completing measurement in the first correction mode, the mode setter 610 may generate a control signal for setting an operation mode of the bio-signal measuring apparatus 600 to the second correction mode. In this manner, the impedance measurer 130 may be connected to the first circuit network of the circuit network part 120 in the first correction mode to measure the first impedance of the first circuit network and may be connected to the second circuit network of the circuit network part 120 in the second correction mode to measure the second impedance of the second circuit network. Further, the parameter obtainer 140 may obtain an internal parameter of the impedance measurer 130, based on the first impedance and the second impedance.

The mode setter 610 may generate a control signal for setting an operation mode of the bio-signal measuring apparatus 600 to the first measurement mode according to a predetermined cycle, a user's instruction, a specific event (e.g., completing obtaining the internal parameter of the impedance measurer 130, etc.), and the like. Upon completing measurement in the first measurement mode, the mode setter 610 may generate a control signal for setting an operation mode of the bio-signal measuring apparatus 600 to the second measurement mode. In this manner, the impedance measurer 130 may be connected to the electrode part 110 in the first measurement mode to measure the third impedance of the object and may measure the fourth impedance of the object in the second measurement mode. Further, the bio-impedance obtainer 150 may obtain the bio-impedance of the object based on the third impedance, the fourth impedance, and the internal parameter of the impedance measurer 130, which is obtained in the first and second correction modes.

The bio-information obtainer 620 may obtain bio-information of the object based on the bio-impedance of the object. In this case, the bio-information may include at least one health diagnostic: including but not limited to body fat mass, fat-free mass, muscle mass, skeletal muscle mass, basal metabolism, intracellular water, extracellular water, total body water, mineral content, visceral fat, blood flow, respiration, heart rate, heart rate variability, and the like.

In one embodiment, the bio-information obtainer 620 may obtain the bio-information of the object by using a bio-information calculation formula. In this case, the bio-information calculation formula defines a relationship between the bio-impedance, body information, and bio-information, and may be pre-obtained experimentally, in which the bio-information may include gender, height, weight, and the like.

The input part 630 may receive input of various operation signals from a user. In one embodiment, the input part 630 may include a keypad, a dome switch, a touch pad (static pressure/capacitance), a jog wheel, a jog switch, a hardware (H/W) button, and the like. The touch pad, which forms a layer structure with a display, may be called a touch screen.

The storage part 640 may store programs or instructions for operation of the bio-signal measuring apparatus 600, and may store data input to and output from the bio-signal measuring apparatus 600. Further, the storage part 640 may store the impedance (including the impedance for each frequency) measured by the impedance measurer 130, the internal parameter (including the internal parameter for each frequency) of the impedance measurer 130, which is obtained by the parameter obtainer 140, the bio-impedance obtained by the bio-impedance obtainer 150, the bio-information obtained by the bio-information obtainer 620, the bio-impedance estimation equation, the bio-information estimation equation, and the like.

The storage part 640 may include at least one storage medium: a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EE-PROM), a Programmable Read Only Memory (PROM), a magnetic memory, a magnetic disk, an optical disk, and the like. Further, the bio-signal measuring apparatus 600 may operate an external storage medium, such as web storage and the like, which performs a storage function of the storage part 640 on the Internet.

The communicator 650 may perform communication with an external device. For example, the communicator 650 may transmit, to the external device, data input from a user through the input part 630, the impedance (including the impedance for each frequency) measured by the impedance measurer 130, the internal parameter (including the internal parameter for each frequency) of the impedance measurer 130, which is obtained by the parameter obtainer 140, the bio-impedance obtained by the bio-impedance obtainer 150, the bio-information obtained by the bio-information obtainer 620, the bio-impedance estimation equation, the bio-information estimation equation, and the like; or may receive, from the external device, various data for obtaining the bio-impedance and/or bio-information.

In this case, the external device may be medical equipment using the data input from a user through the input part 630, the impedance (including the impedance for each frequency) measured by the impedance measurer 130, the internal parameter (including the internal parameter for each frequency) of the impedance measurer 130, which is obtained by the parameter obtainer 140, the bio-impedance obtained by the bio-impedance obtainer 150, the bio-information obtained by the bio-information obtainer 620, the bio-impedance estimation equation, the bio-information estimation equation, and the like, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation system, an MP3 player, a digital camera, a wearable device, and the like, but is not limited thereto.

The communicator 650 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is not intended to be limiting.

The output part 660 may output the data input from a user through the input part 630, the impedance (including the impedance for each frequency) measured by the impedance measurer 130, the internal parameter (including the internal parameter for each frequency) of the impedance measurer 130, which is obtained by the parameter obtainer 140, the bio-impedance obtained by the bio-impedance obtainer 150, the bio-information obtained by the bio-information obtainer 620, the bio-impedance estimation equation, the bio-information estimation equation, and the like. In one embodiment, the output part 660 may output the data input from a user through the input part 630, the impedance (including the impedance for each frequency) measured by the impedance measurer 130, the internal parameter (including the internal parameter for each frequency) of the impedance measurer 130, which is obtained by the parameter obtainer 140, the bio-impedance obtained by the bio-impedance obtainer 150, the bio-information obtained by the bio-information obtainer 620, the bio-impedance estimation equation, the bio-information estimation equation, and the like by using any one or any combination of an acoustic method, a visual method, and a tactile method. To this end, the output part 660 may include a display, a speaker, a vibrator, and the like.

Figure 7:
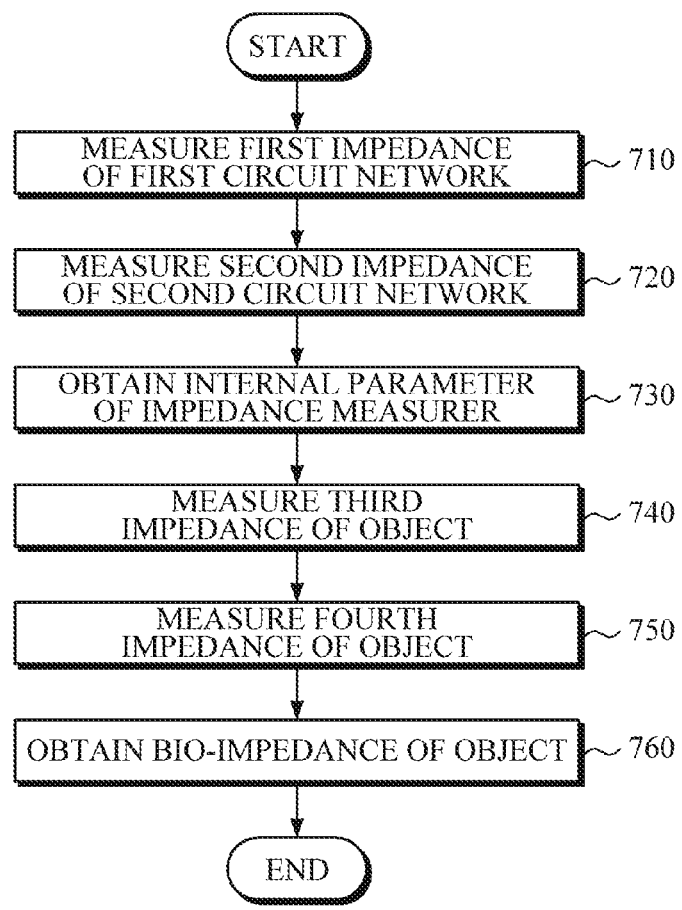
FIG. 7 is a flowchart illustrating an example of a bio-signal measuring method.

FIG. 7 is a flowchart illustrating an example of a bio-signal measuring method. The bio-signal measuring method of FIG. 7 may be performed by the bio-signal measuring apparatus 100 of FIG. 1.

Referring to FIGS. 1 and 7, the bio-signal measuring apparatus 100 may measure the first impedance of the first circuit network in the first correction mode in 710. For example, upon entering the first correction mode, the bio-signal measuring apparatus 100 may connect the four terminals, the first terminal through the fourth terminal, of the impedance measurer 130 to the first circuit network 121; may apply a current to the first circuit network 121 through the first terminal and the second terminal; and may measure a voltage produced by the applied current between the third terminal and the fourth terminal. Further, the bio-signal measuring apparatus 100 may obtain the first impedance of the first circuit network 121 by using a relational expression, $V=I \times Z$, between the voltage V, the current I, and the impedance Z.

The bio-signal measuring apparatus 100 may measure the second impedance of the second circuit network in the second correction mode in 720. For example, upon completing measurement of the first impedance of the first circuit network 121, the bio-signal measuring apparatus 100 may enter the second correction mode, may connect the four terminals, the first terminal through the fourth terminal, of the impedance measurer 130 to the second circuit network 122, may apply a current to the second circuit network 122 through the first terminal and the second terminal, and may measure a voltage produced by the applied current between the third terminal and the fourth terminal. Further, the bio-signal measuring apparatus 100 may obtain the second impedance of the second circuit network 122 by using a relational expression, $V=I \times Z$, between the voltage V, the current I, and the impedance Z.

The first circuit network 121 and the second circuit network 122 each may include at least one or more resistances. Further, the first circuit network 121 and the second circuit network 122 may be implemented separately as independent circuits, and may be configured as a single circuit, the structure of which may be changed by an internal switch and the like. In the case in which the first circuit network 121 and the second circuit network 122 are configured as a single circuit, the structure of which may be changed, and when the bio-signal measuring apparatus 100 enters the second correction mode, connection of the four terminals of the impedance measurer 130 to the first circuit network 121 may be changed to the second circuit network 122 by changing the structure of the circuit.

The bio-signal measuring apparatus 100 may obtain an internal parameter of the impedance measurer 130 based on the first impedance of the first circuit network 121 and the second impedance of the second circuit network 122 in 730. Here, the internal parameter may include the input impedance and the output impedance. For example, the bio-signal measuring apparatus 100 may obtain the internal parameter of the impedance measurer 130 by using the first impedance relational expression, the second impedance relational expression, and the first impedance value and the second impedance value.

The bio-signal measuring apparatus 100 may measure the third impedance of an object in the first measurement mode in 740. For example, upon entering the first measurement mode, the bio-signal measuring apparatus 100 may connect the four terminals, the first terminal through the fourth terminal, of the impedance measurer 130 to the four electrodes 111 through 114 of the electrode part 110; may apply a current to the object through the first electrode 111 and the second electrode 112; and may measure a voltage produced by the applied current between the third electrode 113 and the fourth electrode 114. Further, the bio-signal measuring apparatus 100 may obtain the third impedance of the object by using a relational expression, $V=I \times Z$, between the voltage V, the current I, and the impedance Z.

The bio-signal measuring apparatus 100 may measure the fourth impedance of the object in the second measurement mode in 750. For example, upon completing measurement of the third impedance of the object in the first measurement mode, the bio-signal measuring apparatus 100 enters the second measurement mode, and short-circuits the first electrode 111 to the third electrode 113 and short-circuits the second electrode 112 to the fourth electrode 114. Further, the bio-signal measuring apparatus 100 may apply a current to the object through the first electrode 111 and the second electrode 112; may measure a voltage produced by the applied current between the third electrode 113 and the fourth electrode 114; and may obtain the fourth impedance of the object by using a relational expression, $V=I \times Z$, between the voltage V, the current I, and the impedance Z.

The bio-signal measuring apparatus 100 may obtain the bio-impedance of the object by using the internal parameter (e.g., the input impedance and the output impedance) of the impedance measurer 130, the third impedance, and the fourth impedance in 760. For example, the bio-signal measuring apparatus 100 may obtain the bio-impedance of the object by using a bio-impedance calculation formula which defines a relationship between the internal parameter of the impedance measurer 130, the third impedance, the fourth impedance, and the bio-impedance. For example, the bio-impedance calculation formula may be represented by the Equation 1.

In one embodiment, the bio-signal measuring apparatus 100 may measure the first impedance of the first circuit network 121 and the second impedance of the second circuit network 122 by changing a frequency of an input current. In this case, the bio-signal measuring apparatus 100 may obtain an internal parameter for each frequency of the impedance measurer 130 based on the first impedance and the second impedance, which are measured for each frequency; and may use the internal parameter for each frequency of the impedance measurer 130 to obtain the bio-impedance for each frequency.

Figure 8:
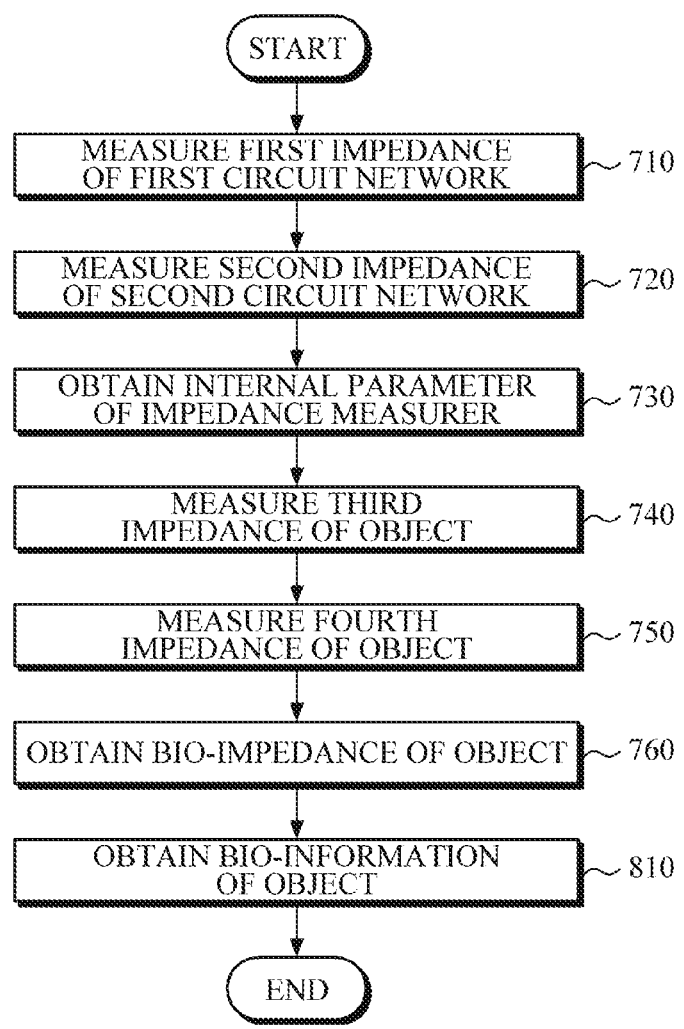
FIG. 8 is a flowchart illustrating another example of a bio-signal measuring method.

FIG. 8 is a flowchart illustrating another example of a bio-signal measuring method. The bio-signal measuring method of FIG. 8 may be performed by the bio-signal measuring apparatus 600 of FIG. 6. In description of FIG. 8, operations 710 to 760 are described above with reference to FIG. 7 such that detailed description thereof will be omitted.

Referring to FIGS. 6 to 8, the bio-signal measuring apparatus 600 may measure the first impedance of the first circuit network in the first correction mode in 710.

The bio-signal measuring apparatus 600 may measure the second impedance of the second circuit network in the second correction mode in 720.

The bio-signal measuring apparatus 600 may obtain the internal parameter of the impedance measurer 130, based on the first impedance of the first circuit network 121 and the second impedance of the second circuit network 122 in 730.

The bio-signal measuring apparatus 600 may measure the third impedance of the object in the first measurement mode in 740.

The bio-signal measuring apparatus 600 may measure the fourth impedance of the object in the second measurement mode in 750.

The bio-signal measuring apparatus 600 may obtain bio-information of the object based on the bio-impedance of the object in 810. In this case, the bio-information may include at least one health diagnostic: including but not limited to body fat mass, fat-free mass, muscle mass, skeletal muscle mass, basal metabolism, intracellular water, extracellular water, total body water, mineral content, visceral fat, blood flow, respiration, heart rate, heart rate variability, and the like. For example, the bio-signal measuring apparatus 600 may obtain bio-information of the object by using the bio-information calculation formula which defines a relationship between the bio-impedance, body information, and bio-information, in which the bio-information may include gender, height, weight, and the like.

The disclosure can be realized as a computer-readable code written on a computer-readable recording medium. Codes and code segments used for realizing the disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

The foregoing embodiments are examples and are not to be construed as limiting. The present teaching can be readily applied to other types of apparatuses. Also, the description of the embodiments is intended to be illustrative, and not to limit the scope of the claims, and many alternatives, modifications and variations will be apparent to those skilled in the art.

What is claimed is:

1. A bio-signal measuring apparatus, comprising:
a first electrode;
a second electrode;
a third electrode;
a fourth electrode;
a first circuit network and a second circuit network, each of the first circuit network and the second circuit network includes one or more resistances;
an impedance measuring circuit configured to:
measure a first impedance of the first circuit network in a first correction mode in which the one or more resistances having known values are connected;
measure a second impedance of the second circuit network in a second correction mode in which the one or more resistances connected in the first correction mode, are disconnected by closing a switch that forms a bypass current path of each of the one or more resistances;
measure a body impedance of an object in a measurement mode, using the first electrode, the second electrode, the third electrode, and the fourth electrode; and
a processor configured to:
obtain an internal parameter of the impedance measuring circuit, based on the first impedance of the first circuit network in the first correction mode and the second impedance of the second circuit network in the second correction mode; and
obtain a bio-impedance of the object, based on the internal parameter, and the body impedance of the object in the measurement mode.

2. The bio-signal measuring apparatus of claim 1, wherein the first circuit network and the second circuit network are configured as a single circuit.

3. The bio-signal measuring apparatus of claim 1, wherein the first circuit network and the second circuit network are configured separately as independent circuits.

4. The bio-signal measuring apparatus of claim 1, wherein in the first correction mode, the impedance measuring circuit is connected to the first circuit network and further configured to:
apply a current to the first circuit network through a first terminal corresponding to the first electrode and a second terminal corresponding to the second electrode; and
measure the first impedance by measuring a voltage produced between a third terminal corresponding to the third electrode and a fourth terminal corresponding to the fourth electrode.

5. The bio-signal measuring apparatus of claim 1, wherein in the second correction mode, the impedance measuring circuit is connected to the second circuit network and further configured to:
apply a current to the second circuit network through a first terminal corresponding to the first electrode and a second terminal corresponding to the second electrode; and
measure the second impedance by measuring a voltage produced between a third terminal corresponding to the third electrode and a fourth terminal corresponding to the fourth electrode.

6. The bio-signal measuring apparatus of claim 1, wherein the measurement mode is a first measurement mode that uses a four-point measurement method of using the first electrode, the second electrode, the third electrode, and the fourth electrode,
the impedance measuring circuit is further configured to measure the body impedance of the object in a second measurement mode that uses a two-point measurement method of measuring an impedance, using short-circuits of a combination of the first electrode, the second electrode, the third electrode, and the fourth electrode, and
the processor is further configured to obtain the bio-impedance of the object, based on the internal parameter, the body impedance of the object that is measured in the first measurement mode and the second measurement mode.

7. The bio-signal measuring apparatus of claim 1, wherein in the measurement mode, the impedance measuring circuit is connected to the first electrode, the second electrode, the third electrode, and the fourth electrode, and further configured to:
apply a current to the object through the first electrode and the second electrode; and
measure the body impedance by measuring a voltage produced between the third electrode and the fourth electrode.

8. The bio-signal measuring apparatus of claim 1, wherein the measurement mode is a first measurement mode, and the impedance measuring circuit is further configured to measure the body impedance of the object in a second measurement mode,
in the second measurement mode, the impedance measuring circuit is connected to the first electrode, the second electrode, the third electrode, and the fourth electrode, short-circuits the first electrode to the third electrode and short-circuits the second electrode to the fourth electrode, and is further configured to:
apply a current to the object through the first electrode and the second electrode; and
measure the body impedance by measuring a voltage produced between the third electrode and the fourth electrode, wherein the processor is further configured to obtain the bio-impedance of the object, based on the internal parameter, and the body impedance of the object that is measured in the first measurement mode and the second measurement mode.

9. The bio-signal measuring apparatus of claim 1, wherein the internal parameter comprises an input impedance and an output impedance.

10. The bio-signal measuring apparatus of claim 1, wherein the processor is further configured to use a bio-impedance calculation formula defining a relationship between the internal parameter of the impedance measuring circuit, the body impedance, and the bio-impedance.

11. The bio-signal measuring apparatus of claim 10, wherein the bio-impedance calculation formula is obtained by measuring a contact impedance when each electrode contacts the object.

12. The bio-signal measuring apparatus of claim 1, wherein the impedance measuring circuit is further configured to measure the first impedance and the second impedance by changing a frequency of an input current.

13. The bio-signal measuring apparatus of claim 12, wherein the processor is further configured to obtain the internal parameter for each frequency of the impedance measuring circuit, based on the first impedance and the second impedance that are measured for each frequency of the input current.

14. The bio-signal measuring apparatus of claim 13, further comprising a memory configured to store the internal parameter for each frequency of the impedance measuring circuit.

15. The bio-signal measuring apparatus of claim 1, wherein the processor is further configured to generate a control signal for setting an operation mode of the bio-signal measuring apparatus.

16. The bio-signal measuring apparatus of claim 1, wherein the processor is further configured to obtain bio-information of the object based on the bio-impedance of the object.

17. The bio-signal measuring apparatus of claim 16, wherein the bio-information comprises any one or any combination of body fat mass, fat-free mass, muscle mass, skeletal muscle mass, basal metabolism, intracellular water, extracellular water, total body water, mineral content, visceral fat, blood flow, respiration, heart rate, and heart rate variability.

18. A bio-signal measuring method, comprising:
measuring a first impedance of a first circuit network in a first correction mode of an impedance measuring circuit in which one or more resistances having known values are connected;
measuring a second impedance of a second circuit network in a second correction mode of the impedance measuring circuit, in which the one or more resistances connected in the first correction mode, are disconnected by closing a switch that forms a bypass current path of each of the one or more resistances;
obtaining an internal parameter of the impedance measuring circuit, based on the first impedance of the first circuit network in the first correction mode and the second impedance of the second circuit network in the second correction mode;
measuring a body impedance of an object in a measurement mode; and
obtaining a bio-impedance of the object, based on the internal parameter, and the body impedance of the object that is measured in the measurement mode.

19. The method of claim 18, wherein each of the first circuit network and the second circuit network includes the one or more resistances.

20. The method of claim 18, wherein the first circuit network and the second circuit network are configured as a single circuit.

21. The method of claim 18, wherein the first circuit network and the second circuit network are configured separately as independent circuits.

22. The method of claim 18, wherein the measuring of the first impedance comprises:
entering the first correction mode;
connecting the impedance measuring circuit to the first circuit network;
applying a current to the first circuit network through a first terminal and a second terminal of the impedance measuring circuit;
measuring a voltage produced between a third terminal and a fourth terminal of the impedance measuring circuit; and
obtaining the first impedance based on the current and the voltage.

23. The method of claim 18, wherein the measuring of the second impedance comprises:
based on the measuring the first impedance being completed, entering the second correction mode;
connecting the impedance measuring circuit to the second circuit network;
applying a current to the first circuit network through a first terminal and a second terminal of the impedance measuring circuit;
measuring a voltage produced between a third terminal and a fourth terminal of the impedance measuring circuit; and
obtaining the second impedance based on the current and the voltage.

24. The method of claim 18, wherein the measurement mode is a first measurement mode that uses a four-point measurement method of using four electrodes;
the measuring the body impedance comprises measuring the body impedance of the object in the first measurement mode, and in a second measurement mode that uses a two-point measurement method of using short-circuits of a combination of the four electrodes; and
the obtaining the bio-impedance of the object comprises obtaining the bio-impedance based on the internal parameter, and the body impedance of the object that is measured in the first measurement mode and the second measurement mode.

25. The method of claim 18, wherein the measuring of the body impedance comprises:
entering the first correction mode;
connecting a first terminal of the impedance measuring circuit to a first electrode, a second terminal of the impedance measuring circuit to a second electrode, a third terminal of the impedance measuring circuit to a third electrode, and a fourth terminal of the impedance measuring circuit to a fourth electrode;
applying a current to the object through the first electrode and the second electrode;
measuring a voltage produced between the third electrode and the fourth electrode; and
obtaining the body impedance based on the current and the voltage.

26. The method of claim 18, wherein the measurement mode is
a first measurement mode that uses a four-point measurement method of using four electrodes;
the measuring the body impedance comprises measuring the body impedance of the object in the first measurement mode, and in a second measurement mode that uses a two-point measurement method of using short-circuits of a combination of the four electrodes;

the measuring of the body impedance in the second measurement mode, comprises:
based on the measuring the body impedance in the first measurement mode being completed, entering the second measurement mode;
short-circuiting a first electrode to a third electrode, and short-circuiting a second electrode to a fourth electrode;
applying a current to the object through the first electrode and the second electrode;
measuring a voltage produced between the third electrode and the fourth electrode; and
obtaining the body impedance in the second measurement mode based on the current and the voltage.

27. The method of claim 18, wherein the internal parameter comprises an input impedance and an output impedance.

28. The method of claim 18, wherein the obtaining of the bio-impedance of the object comprises obtaining the bio-impedance of the object by using a bio-impedance calculation formula which defines a relationship between the internal parameter of the impedance measuring circuit, the body impedance, and the bio-impedance.

29. The method of claim 28, wherein the bio-impedance calculation formula is obtained by considering a contact impedance, which occurs when each electrode contacts the object.

30. The method of claim 18, further comprising obtaining bio-information of the object based on the bio-impedance of the object.

31. The method of claim 30, wherein the bio-information comprises any one or any combination of body fat mass, fat-free mass, muscle mass, skeletal muscle mass, basal metabolism, intracellular water, extracellular water, total body water, mineral content, visceral fat, blood flow, respiration, heart rate, and heart rate variability.

* * * * *